US 7,963,980 B1
Jun. 21, 2011

(12) United States Patent
Freeman et al.

(54) CERVICAL PLATE SYSTEM (75) Inventors: Thomas B. Freeman, Tampa, FL (US); Wesley Johnson, Tampa, FL (US)

(73) Assignee: University of South Florida, Tampa, FL (US)

( * ) Notice: Subject to any disclaimer, the term of this patent is extended or adjusted under 35 U.S.C. 154(b) by 508 days.

(21) Appl. No.: 11/736,627

(22) Filed: Apr. 18, 2007

Related U.S. Application Data (60) Provisional application No. 60/745,025, filed on Apr. 18, 2006.

(51) Int. Cl.
*A61B 17/80* (2006.01)

(52) U.S. Cl. .......................... 606/286; 606/280; 606/287

(58) Field of Classification Search .................. 606/280, 606/914, 61, 69, 295, 282, 286, 287
See application file for complete search history.

(56) References Cited

U.S. PATENT DOCUMENTS

| | | | |
|---|---|---|---|
| 4,095,591 A | 6/1978 | Graham, Jr. et al. | |
| 5,364,399 A * | 11/1994 | Lowery et al. | 606/295 |
| 5,423,826 A | 6/1995 | Coates et al. | |
| 5,681,311 A | 10/1997 | Foley et al. | |
| 5,904,683 A | 5/1999 | Pohndorf et al. | |
| 6,017,345 A | 1/2000 | Richelsoph | |
| 6,342,057 B1 * | 1/2002 | Brace et al. | 606/96 |
| 6,379,364 B1 | 4/2002 | Brace et al. | |
| 6,398,783 B1 | 6/2002 | Michelson | |
| 6,454,771 B1 * | 9/2002 | Michelson | 606/70 |
| 6,599,290 B2 | 7/2003 | Bailey et al. | |
| 6,652,525 B1 | 11/2003 | Assaker et al. | |
| 6,692,503 B2 | 2/2004 | Foley et al. | |
| 6,936,051 B2 | 8/2005 | Michelson | |
| 6,969,390 B2 | 11/2005 | Michelson | |
| 6,989,012 B2 * | 1/2006 | LeHuec et al. | 606/914 |
| 7,001,387 B2 | 2/2006 | Farris et al. | |
| 7,011,665 B2 | 3/2006 | Null et al. | |
| 7,081,119 B2 | 7/2006 | Stihl | |
| 7,527,640 B2 * | 5/2009 | Ziolo et al. | 606/288 |
| 2001/0047172 A1 * | 11/2001 | Foley et al. | 606/69 |
| 2002/0147450 A1 * | 10/2002 | LeHuec et al. | 606/61 |
| 2004/0097925 A1 | 5/2004 | Boehm, Jr. et al. | |
| 2004/0204716 A1 | 10/2004 | Fanger et al. | |
| 2005/0015093 A1 | 1/2005 | Suh et al. | |
| 2005/0075633 A1 | 4/2005 | Ross | |
| 2005/0149026 A1 | 7/2005 | Butler et al. | |
| 2006/0079901 A1 * | 4/2006 | Ryan et al. | 606/69 |
| 2006/0200134 A1 * | 9/2006 | Freid et al. | 606/61 |

* cited by examiner

*Primary Examiner* — Eduardo C Robert
*Assistant Examiner* — Andrew Yang
(74) *Attorney, Agent, or Firm* — Jeremy Spier; Smith & Hopen, P.A.

(57) ABSTRACT

An anti-subsidence, anti-translocation, fusion compression cervical plate system with interface visualization, drill guide and temporary pin is provided. In one embodiment the invention provides a vertebral plate for minimizing the ability of an inter-body cage, filled with bone (or BMP-soaked sponges, etc.), to telescope into the vertebral body and to minimize failure due to cages that telescope into adjacent vertebral bodies on a delayed basis after surgery, as well as creation of reverse lordosis due to such telescoping. Another embodiment provides method to reduce the gap between the inter-body cage and the vertebral body end plate intra-operatively using compression from the plate caused by an offset between the screw bores on the plate and the drill holes, as established with an asymmetric drill guide.

19 Claims, 7 Drawing Sheets

CERVICAL PLATE SYSTEM

CROSS REFERENCE TO RELATED APPLICATIONS

This application is a non-provisional of U.S. Provisional Application 60/745,025, filed Apr. 18, 2006; which is incorporated herein by reference.

FIELD OF THE INVENTION

The invention relates to the field of surgery, more specifically to surgery of the cervical spine. It should be understood, however, that vertebrae other than the cervical vertebrae of the human spine may be retained with the disclosed apparatus and associated methods.

BACKGROUND OF THE INVENTION

Anterior cervical discectomy with fusion is an operation that involves relieving the pressure placed on nerve roots and the spinal cord by a herniated disc or bone spurs. This condition is referred to as nerve root compression. The procedure includes removing the damaged intervertebral disc, which is usually the source of the compression and placing a bone graft between vertebrae adjacent to the space left by the removed disc. The bone graft is commonly an inter-vertebral-body cage filled with bone (or BMP-soaked sponges, etc.). Commonly, a vertebral plate is used to stabilize the spine and contain the intra-body cage while the spine heals.

There are currently numerous plates used for the process of internal fixation in the cervical spine. Some have locking screws and some have variable angle or axis screws and others have a mixture of both of the above. A common problem with the use of any cervical plate in conjunction with inter-body cages is that the cages telescope or subside into adjacent vertebral bodies on a delayed basis after surgery. This is due to a variety of factors including differences in biomechanical properties of the cage in relation to the vertebral body, inadvertent destruction of the end plate during end plate preparation, poor bone quality and micromotion, among others. If subsidence becomes too great, screws will break and the plate will fail.

A second problem is that the superior vertebral body may translocate anteriorly on a rotational basis, with the anterior inferior cage serving as the fulcrum; anterior rotational translocation. Even with locking screws in the inferior aspect of current plates, this anterior rotational translocation is not prevented.

A third method of cage and fusion failure is due to inadvertent creation of a gap between the interbody cage filled with bone (or BMP-soaked sponges, etc.) and the vertebral body end plate. A method to reduce this gap intraoperatively, using a ("lag screw") compression from the plate to the vertebral body that reduces this gap, would minimize this problem. In addition, compression across a fusion mass is known to increase fusion rate, as bone fuses under compressive loads at a higher rate.

SUMMARY OF INVENTION

The invention includes an anti-subsidence, anti-translocation, fusion compression cervical plate system with interface visualization, drill guide and temporary pin. In one embodiment the invention provides a vertebral plate for minimizing the ability of an inter-body cage, filled with bone (or BMP-soaked sponges, etc.), to telescope into the vertebral body and to minimize failure due to cages that telescope into adjacent vertebral bodies on a delayed basis after surgery, as well as creation of reverse lordosis due to such telescoping. Another embodiment provides method to reduce the gap between the inter-body cage and the vertebral body end plate intra-operatively using compression from the plate caused by an offset between the screw bores on the plate and the drill holes, as established with an asymmetric drill guide.

In a first embodiment, the invention includes a vertebral plate which can be used with or without an inter-body cage. The plate includes a first plurality of bone screw bores disposed at the superior end of the frame. A second plurality of bone screw bores, preferably two, is disposed at the inferior end of the frame with a third, locking bone screw bore. The second plurality of bone screw bores comprises two proximal bone screw bores, relative to the inferior end of the inter-body cage, and the locking bone screw bore is a distal bone screw bore.

The two proximal bone screw bores are adapted to aim a bone screw in a caudal direction and the distal bone screw bore is adapted to aim a bone screw in a cephalad direction, parallel to the disc space. The distal bone screw is between the proximal bone screw bores in a preferred embodiment.

In another embodiment, the second plurality of bone screw bores comprises two distal bone screw bores and one proximal locking bone screw bore. In this embodiment, the two distal bone screw bores are adapted to aim a bone screw in a caudal direction and the proximal bone screw bore is adapted to aim a bone screw in a cephalad direction; here the proximal bone screw is between the proximal bone screw bores.

The vertebral plate can also be equipped with a window which allows direct visualization of the interface between the cage and the vertebrae. Another embodiment includes a plurality of notches on the lateral edges of the inferior end of the frame to receive a positioning device. Preferably, the notches are superior to the bone screw bores disposed in the inferior end of the frame.

Another embodiment of the invention includes a vertebral plating system for engaging at least two vertebrae with an inter-body cage there between. The system includes a plate having a pair of notches on the inferior end of the frame, a positioning device for placing the plate in position on at least one vertebra, the device having a body with a predetermined notch to receive the plate, and a drill guide. In alternate embodiments, the notch in the body of the positioning device is centered, thereby allowing the plate to accommodate an inter-body cage disposed along the midline of the vertebrae; or the notch in the body of the positioning device is off-center, thereby allowing the plate to accommodate an inter-body cage disposed eccentric to the midline of the vertebrae.

The plate of the vertebral plating system includes three bone screw bores at the inferior end of the plate, including a plurality of bone screw bores and a locking bone screw bore. The plurality of bone screw bores comprises two proximal bone screw bores adapted to aim a bone screw in a first direction and the locking bone screw bore is a distal bone screw bore adapted to aim a bone screw in a second direction. Alternatively, the plurality of bone screw bores comprises two distal bone screw bores adapted to aim a bone screw in a first direction, and the locking bone screw bore is a distal bone screw bore adapted to aim a bone screw in a second direction.

An alternate vertebral plating system for engaging at least two vertebrae with an inter-body cage there between includes a plate having a superior and an inferior end, a first plurality of bone screw bores disposed at the superior end of the frame, a second plurality of bone screw bores disposed at the inferior end of the frame, a locking bone screw bore disposed at the inferior end of the frame, a first drill guide having a plurality of guide tubes adapted to engage to the second plurality of bone screw bores in the plate, said first drill guide further having a guide tube adapted to engage the locking bone screw bore disposed in the plate, and a second drill guide having a guide tube with an aperture there through, said aperture adapted to be off-center by a predetermined distance whereby the holes drilled the in vertebrae using the second drill guide are asymmetric to the bone screw bores in the plate.

The plurality of guide tubes adapted to engage the second plurality of bone screw bores are adapted to aim a bone screw in a first direction, and the guide tube adapted to engage the locking bone screw bore is adapted to aim a bone screw in a second direction. Alternatively the second plurality of bone screw bores comprises two distal bone screw bores adapted to aim a bone screw in a first direction; and wherein the locking bone screw bore is a distal bone screw bore adapted to aim a bone screw in a second direction.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
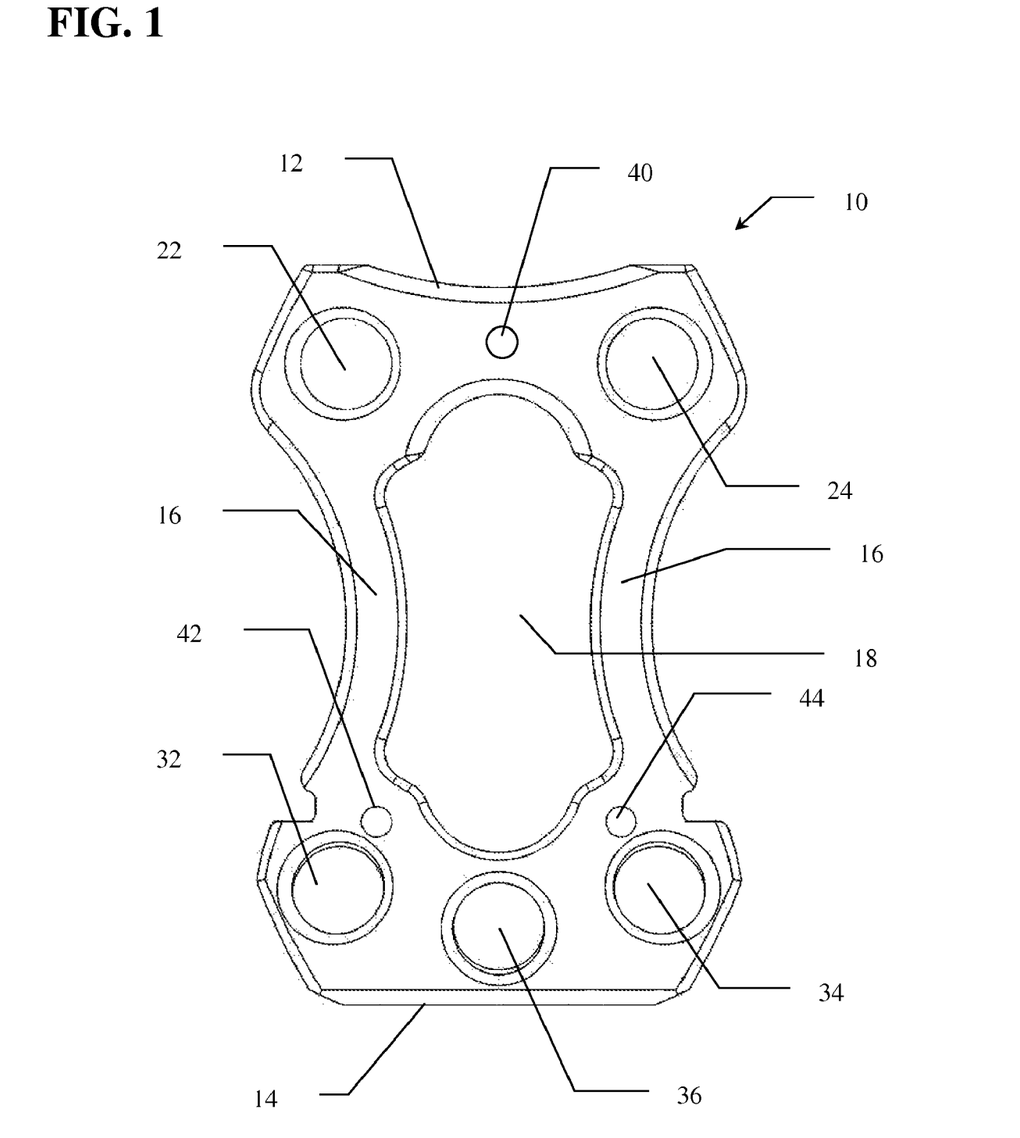
FIG. 1 is a front perspective view of the vertebral plate.

Referring to FIG. 1, the cervical stabilization plate (10) of the present invention is shown. In use, plate 10 is positioned between at least two vertebrae, above and below the disc to be treated and/or removed. In the preferred embodiment, plate 10 has a substantially hour-glass shaped frame having superior end 12 and inferior end 14 spaced at a predetermined distance by arms 16. Window 18 is defined by the open space between superior end 12, inferior end 14 and arms 16. Window 18 allows for direct visualization of the interface between the inferior aspect of the inter-body cage and the superior aspect of the inferior end plate.

Superior end 12 includes temporary pin-hole 40, at the center position thereof, for receiving a temporary positioning screw. Superior end 12 also includes bone screw bores 22 and 24, which are preferably located on either side of the midline of plate 10, for fixing the superior end of plate 10 to the vertebrae with bone screws.

Inferior end 14 includes temporary pin-holes 42 and 44, located on either side of the mid line of plate 10, also for receiving temporary positioning screws. In addition, inferior end 14 includes a plurality of bone screw bores including proximal bone screw bores 32, 34 and distal bone screw bore 36. In a preferred embodiment, the bone screw bores of inferior end 14 are disposed at angle to aim the bone screws in a predefined direction. In one embodiment, for example, proximal bone screw bores 32, 34 are disposed to aim a bone screw in a caudal direction and distal bone screw bore 36 is disposed to aim a bone screw in a cephalad direction, parallel to the disk space.

The arrangement of three, or more screws, defines a plane as well resisting moment the arrangement prevents rotational translocation in an anterior direction. The arrangement of FIG. 1, having two proximal screws and one distal screw, accentuates the anti-telescoping properties of the plate. In an alternate embodiment, there is one proximal screw and two distal screws, favoring the antitranslocation properties of the plate.

The screw bores disposed on the inferior end of plate 10 function as locking screws, which serve to resist rotational translocation. In order to allow some subsidence, however, the screw bores of superior end 12 are variable angle screws, forcing the superior aspect of the plate to be the dynamic side of plate 10 and inferior end 14 to be the fixed end. This configuration of inferior fixed screws and superior variable angle screws provides the safest combination of a dynamic plate combined with a prevention of telescoping and anterior rotational translocation since telescoping of the cage into the vertebral body superior to the cage is far more uncommon than telescoping of the cage into the vertebral body below the cage.

Figure 2:
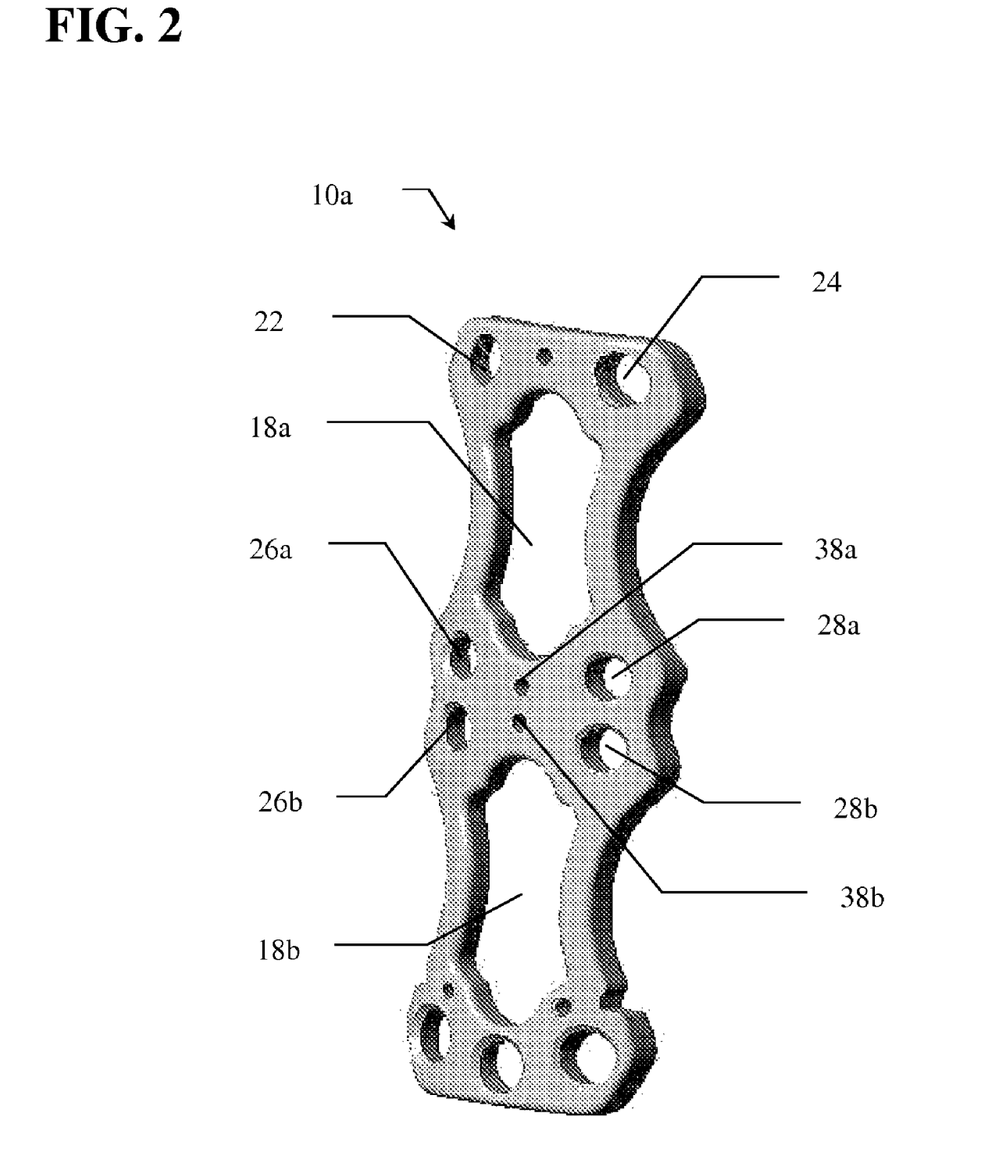
FIG. 2 is an isometric view of a 2-level vertebral plate.

Cervical plate 10a shown in FIG. 2 is a two-level cervical plate have intermediate bone screw bores 26a, 26b, 28a and 28b disposed between superior end 12 and inferior end 14. Additionally, medial frame member 17 is provided between arms 16 to increase rigidity as well as provide for medial temporary pin holes 38a and 38b. Medial frame member 17 also bifurcates window 18 (FIG. 1) to form superior window 18a and inferior window 18b.

Figure 3:
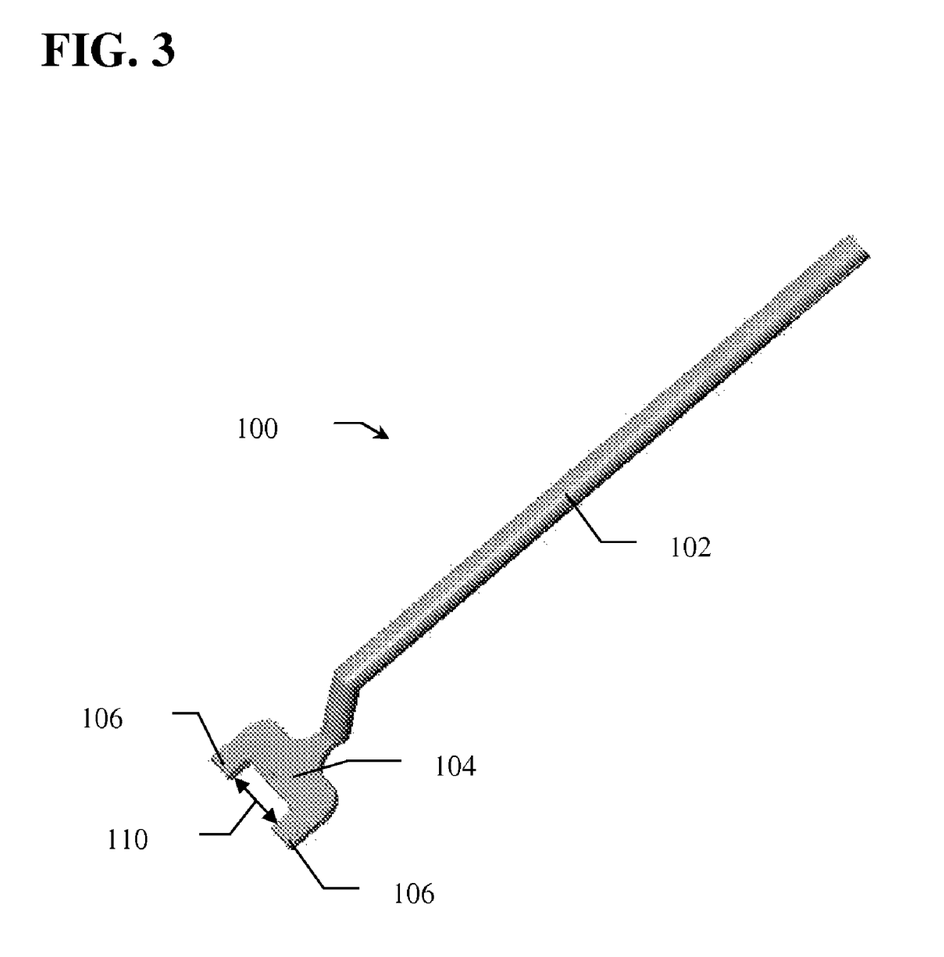
FIG. 3 is an isometric view of a symmetric positioner.
Figure 4A:
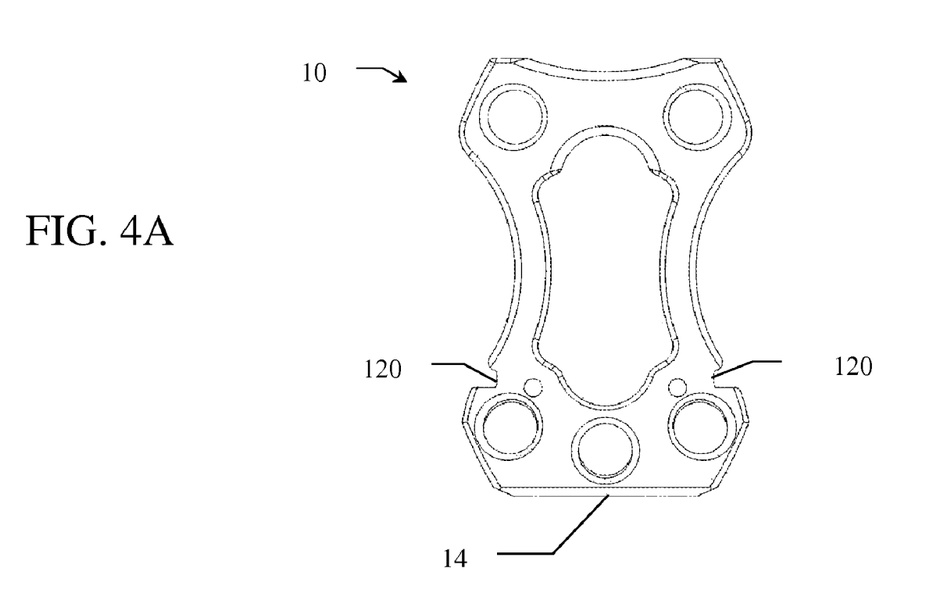
FIG. 4A is a front perspective view of the vertebral plate.
Figure 4B:
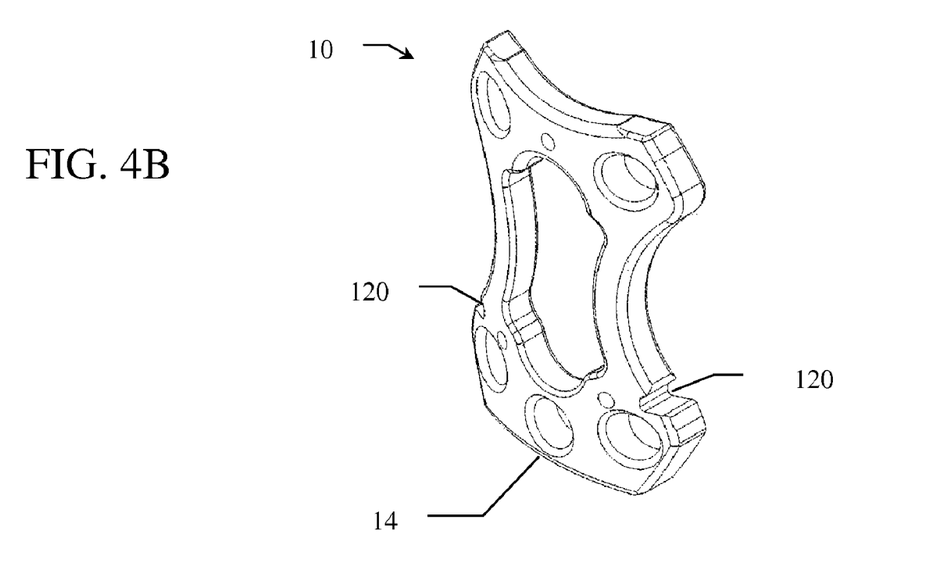
FIG. 4B is an isometric view of the vertebral plate.

In order to prevent the subsidence of the inter-body cage, the invention includes removable plate positioner 100 (FIG. 3). Positioner 100 guarantees a fixed relationship between the inferior screws proximal to the inter-body cage, the vertebral body end plate and the end of the inter-body cage. Positioner 100 comprises handle 102 and substantially flat body 104, from which tines 106 extend to form notch 110. In use, plate 10 is place within notch 110 but inserting tines 106 into positioner notches 120 located on inferior end 14 of plate 10 (FIGS. 4A-4B).

Figure 5:
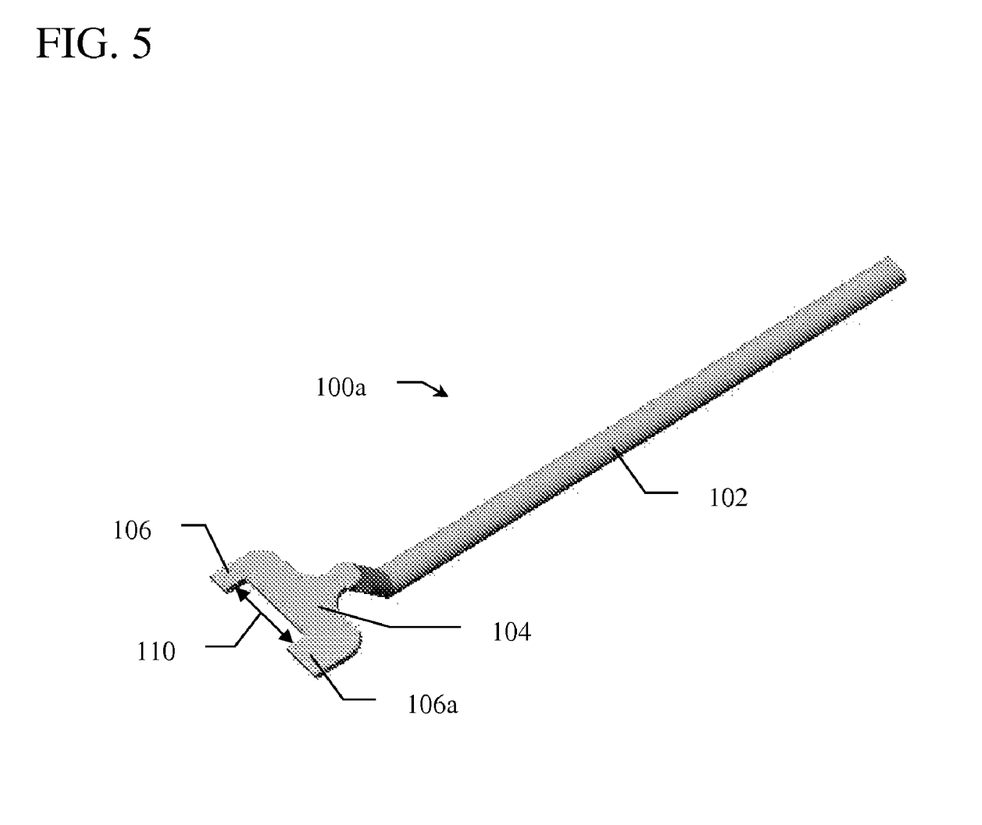
FIG. 5 is an isometric view of an asymmetric positioner.

Tines 106 have a length slightly greater than the width of plate 10, thereby allowing tines 106 to contact the sides of the vertebral body. In the embodiment of FIG. 4, notch 110 is centered in body 104. Accordingly, plate 10 is positioned in a substantially central position when tines 106 are aligned with the sides of the vertebral body. In the embodiment of FIG. 5, however, notch 110a, is off-center to body 104. Here it can be seen that tine 106 has a lesser width than tine 106a. This arrangement allows plate 10 to be positioned eccentric to the midline of the vertebral body when tines 106 are aligned with the sides of the vertebral body. Temporary pin holes 40, 42 and 44 are provided for situations where the positioner cannot be used.

Figure 6:
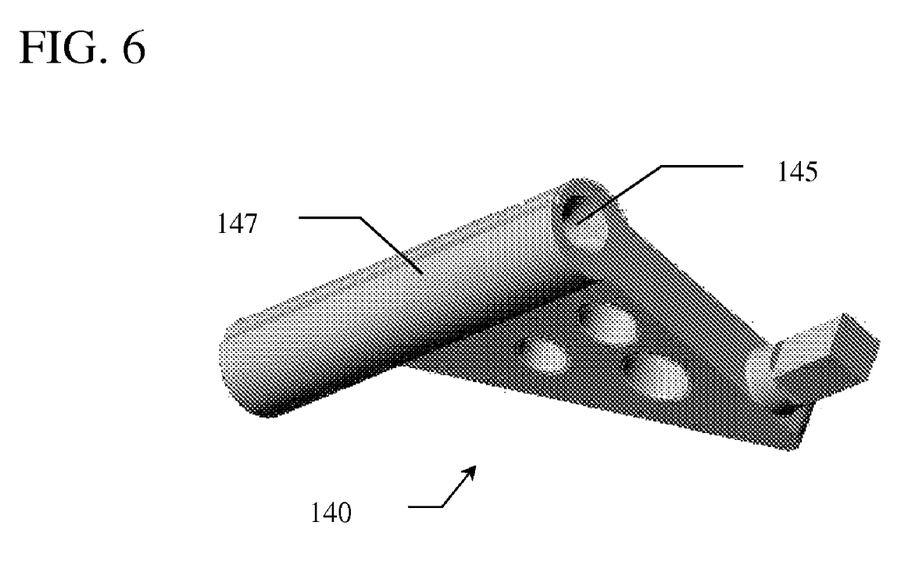
FIG. 6 is an isometric view of an asymmetric drill guide.

Another embodiment of the invention actively compresses across the fusion or inter-body cage by implementing a "lag effect." In one embodiment, shown in FIG. 6, asymmetric drill guide 140 is provided wherein cannula 145 for the drill is located superiorly by a fixed distance off of the center of the guide tube 147. Therefore the holes which are drilled into the vertebral bodies using asymmetric drill guide 140 are off-center (asymmetric) with the bone screw bores in plate 10. Therefore, the process of tightening the bone screws into the vertebral body will create a lag effect, pulling the vertebral bodies tight against the end of the cage.

In another embodiment, compression is achieved by using a temporary pin with an asymmetric spacer to fill the screw hole. This configuration allows manipulation of the inter-body-cage rostrally and caudally as the drilling is performed followed by rostral and column movement of the plate when placing the screws. Here, a standard drill guide is used in a standard hole in plate 10. A temporary pin equipped with a spacer holds plate 10 against the vertebral body. The temporary pin is off-center within the spacer. When the spacer is rotated towards the end of the plate 10, the plate moves away from the inter-body cage. Drilling can then be performed in the contra-lateral hole. Before placing a screw, the spacer is rotated in the opposite direction, bringing the plate in the opposite direction. The hole in the opposite end of the plate is then drilled. This allows the drill holes to be made at a defined distance further apart than the distance between the actual holes on the plate. As the screws are then placed into the vertebral body through the plate, a "lag" effect will be created.

In yet another embodiment, the screw bores of plate 10 are arranged in a figure-eight. The hole created by drilling and the placement of screws are thereby offset by a fixed distance allowing a "lag" effect of that distance. The drill guide is inserted into the distal hole for drilling and the screw is placed in the more proximal hole on the plate. As the screw follows the path of the drill guide, this similarly creates a "lag" effect.

In another embodiment, the drilling is performed through the same hole in which the screw is placed, but the angulation is increased rostral and caudal to the vertical plane in order to create a compression force across the graft in the vertical axis. For example, the upper screw is aimed rostral at a 30° direction and the inferior screw is aimed in a caudal direction by 30°. As the screws are tightened, a "lag" effect is created pulling the vertebral bodies toward the cage by the triangulation of the screws.

Figure 7A:
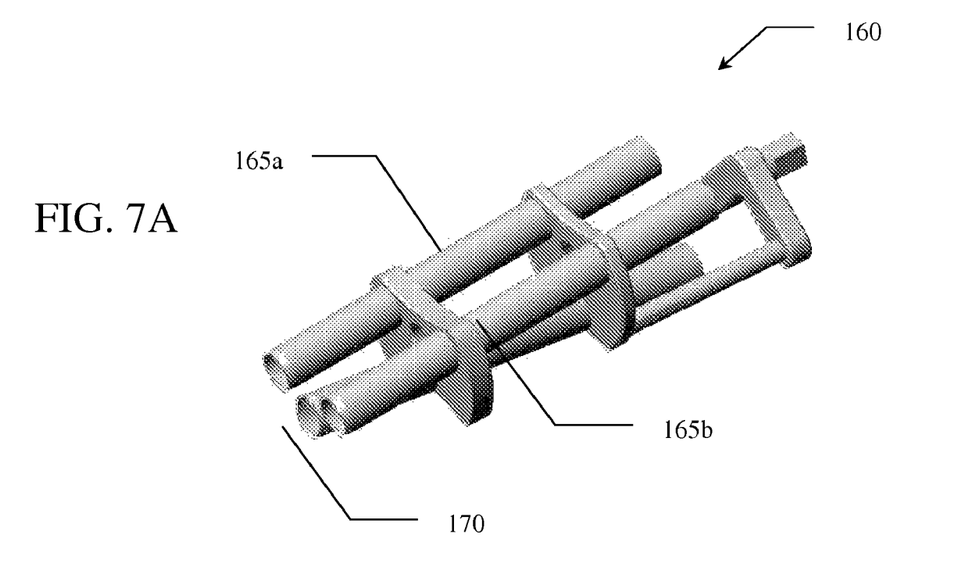
FIG. 7A is an isometric view of a drill guide for use with the inferior end of the vertebral plate.
Figure 7B:
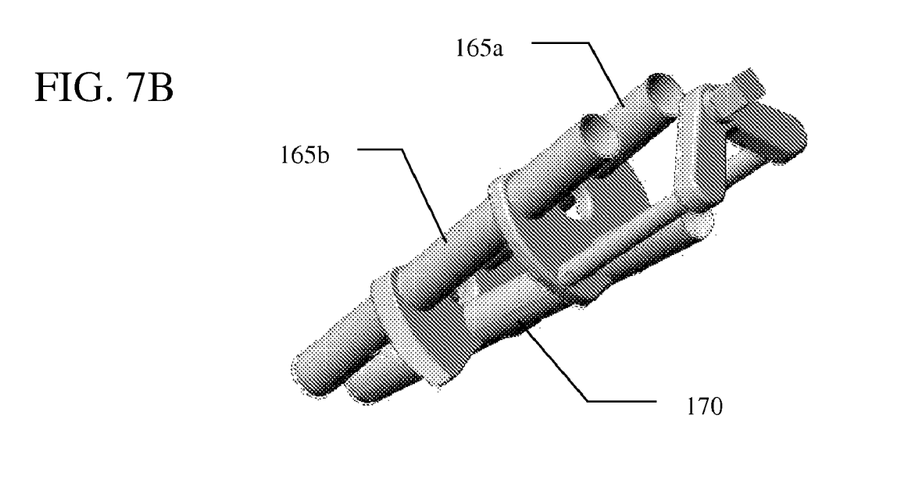
FIG. 7B is an alternate isometric view of a drill guide for use with the inferior end of the vertebral plate.

The invention also include drill guide 160, FIG. 7. Drill guide 160 includes proximal guide tubes 165*a* and 165*b*, and distal guide tube 170. Proximal guide tubes 165*a* and 165*b* are adapted to aim a screw hole in a caudal direction. Distal guide tube 170 is designed to aim a screw hole in a cephalad direction. Drill guide 160 can also be modified for embodiments, as described above, which use two distal screws and a single proximal screw.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A vertebral plate system, comprising:
    a frame having a superior end and an inferior end;
    two bone screw bores disposed at said superior end of said frame;
    three bone screw bores disposed at said inferior end of said frame in a triangular configuration with at least one of said three bone screw bores being disposed on a longitudinal axis of symmetry of said frame;
    two variable angle bone screws disposed within said two bone screw bores at said superior end of said frame;
    three locking bone screws disposed within said three bone screw bores at said inferior end of said frame,
    whereby said superior end of said frame is dynamic and said inferior end of said frame is fixed;
    at least one viewing window disposed within an interior of said frame;
    a plurality of notches formed on said inferior end of said frame, said notches being adapted to receive a positioning device;
    at least one temporary pin hole positioned at said superior end of said frame; and
    at least one temporary pin hole positioned at the inferior end of the frame.

2. A vertebral plate system as in claim 1, wherein said three bone screw bores at said inferior end of said frame includes two proximal bone screw bores and one distal bone screw bore forming a triangular configuration.

3. A vertebral plate system as in claim 2, wherein said two proximal bone screw bores are angled to guide said locking bone screws in a caudal direction.

4. A vertebral plate system as in claim 2, wherein said distal bone screw bore is angled to guide said locking bone screw in a cephalad direction.

5. A vertebral plate system as in claim 2, wherein said distal bone screw bore guides said locking bone screw in parallel relation to a disc space.

6. A vertebral plate system as in claim 2, wherein said distal bone screw bore is positioned between said proximal bone screw bores.

7. A vertebral plate system as in claim 1, wherein three bone screw bores at said inferior end of said frame includes two distal bone screw bores and one proximal bone screw bore forming a triangular configuration.

8. A vertebral plate system as in claim 7, wherein said two distal bone screw bores guide said locking bone screws in a cephalad direction.

9. A vertebral plate system as in claim 7, wherein said proximal bone screw bore guides said locking bone screw in a caudal direction.

10. A vertebral plate system as in claim 7, wherein said distal bone screw bores guide said locking bone screws in parallel relation to a disc space.

11. A vertebral plate system as in claim 7, wherein said proximal bone screw bore is positioned between said distal bone screw bores.

12. A vertebral plate system as in claim 1, wherein said plurality of notches are formed on a periphery of said inferior end of said frame.

13. A vertebral plate system as in claim 1, wherein said plurality of notches are disposed superior to said three bone screw bores disposed at said inferior end of said frame.

14. A vertebral plating system as in claim 1, further comprising:
    a positioning device for placing said frame in position on at least one vertebrae,
    said positioning device having a body with a predetermined slot to receive said frame.

15. A vertebral plating system as in claim 14, where said slot is centered within said body of said positioning device.

16. A vertebral plating system as in claim 14, wherein said slot is off center within said body of said positioning device.

17. A vertebral plating system as in claim 1, further comprising:

a drill guide having a plurality of guide tubes adapted to engage said three bone screw bores in said inferior end of said frame.

18. A vertebral plating system as in claim 1, further comprising:
   a medial frame member disposed between said superior end of said frame and said inferior end of said frame, said medial frame member bifurcates said viewing window; and
   a plurality of bone screw bores disposed at said medial frame member.

19. A vertebral plating system as in claim 1, further comprising:
   at least one temporary pin hole disposed at said medial frame member.

\* \* \* \* \*